(12) United States Patent
Quinn

(10) Patent No.: US 6,436,412 B1
(45) Date of Patent: Aug. 20, 2002

(54) USE OF A HYBRID POLYMERIC MATERIAL FOR COATING KERATINOUS MATERIALS

(75) Inventor: Francis Quinn, Paris (FR)

(73) Assignee: Loreal S.A., Paris (FR)

( * ) Notice: Subject to any disclaimer, the term of this patent is extended or adjusted under 35 U.S.C. 154(b) by 0 days.

(21) Appl. No.: 09/254,424

(22) PCT Filed: Jun. 16, 1998

(86) PCT No.: PCT/FR98/01259

§ 371 (c)(1),
(2), (4) Date: May 19, 1999

(87) PCT Pub. No.: WO99/02127

PCT Pub. Date: Jan. 21, 1999

(30) Foreign Application Priority Data

Jul. 7, 1997 (FR) .............................. 97 08606

(51) Int. Cl.$^7$ ............................ A61K 6/00; A61K 7/00; A61K 7/04; A61K 7/021; A61K 7/025

(52) U.S. Cl. ........................... 424/401; 424/61; 424/63; 424/64; 424/70.1; 424/78.03; 514/944

(58) Field of Search .............................. 424/59, 61, 63, 424/64, 70.1, 70.11, 70.12, 70.13, 70.14, 70.15, 70.16, 70.17, 70.6, 70.7, 401, 78.03; 514/944

(56) References Cited

U.S. PATENT DOCUMENTS

| | | | |
|---|---|---|---|
| 4,506,784 A | | 3/1985 | Keritsis |
| 4,606,913 A | * | 8/1986 | Aronson et al. |
| 4,661,475 A | | 4/1987 | Bayerlein et al. |
| 4,826,700 A | | 5/1989 | Bayerlein et al. |
| 4,897,261 A | * | 1/1990 | Yamazaki et al. |
| 5,683,681 A | * | 11/1997 | Ramin et al. |

FOREIGN PATENT DOCUMENTS

| | | |
|---|---|---|
| DE | 968 469 | 2/1958 |
| DE | 3 222 040 | 1/1983 |
| EP | 0 139 913 | 5/1985 |
| EP | 0 413 418 | 2/1991 |
| EP | 0 432 835 | 6/1991 |
| EP | 0 552 624 | 7/1993 |
| WO | WO 97/18263 | 5/1997 |
| WO | WO 97/49376 | 12/1997 |

OTHER PUBLICATIONS

Patent Abstracts of Japan, vol. 96, No. 001 (JP 07 233045).
Patent Abstracts of Japan, vol. 004, No. 034 (JP 55 009042).
English language Derwent Abstract of DE 3 222 040.

Alex D. Bain et al., "An N.M.R. Study of the Interactions Between Cadoxen and Saccharides", Carbohydrate Research, vol. 84, No. 1, Sep. 8, 1990, pp. 1–12.

Kálmán Burger et al., "Metal complexes of carbohydrates and sugar–type ligands", Biocoordination Chemistry: Coordination Equilibria in Biologically Active Systems, Ch. VI, pp. 236–283.

Robert E. Kesting, Semipermeable Membranes of Cellulose Acetate for Desalination in the Process of Reverse Osmosis. I. Lyotropic Swelling of Secondary Cellulose Acetate*, Journal of Applied Polymer Science, vol. 9, 1965, pp. 668–688.

Vishnu and Vijai P. Misra, "Studies on Electrolyte–Nonelectrolyte Interactions: Viscosity Behavior of Alkali Halides in Aqueous Sucrose Solutions", vol. 59, No. 1, Nov. 1977, pp. 35–46.

J.A. Rendleman, Jr., "Complexes of Alkali Metals and Alkaline–Earth Metals with Carbohydrates", Advances in Carbohydrate Chemistry, vol. 21, 1955, pp. 209–271.

* cited by examiner

Primary Examiner—Thurman K. Page
Assistant Examiner—Humera N. Sheikh
(74) Attorney, Agent, or Firm—Finnegan, Henderson, Farabow, Garrett & Dunner, L.L.P.

(57) ABSTRACT

The invention relates to the use, for coating keratin substances, of a crosslinked hybrid polymer material which can be obtained from an aqueous solution containing:

(a) at least one water-soluble polymer containing at least functional groups capable of forming hydrogen bonds, and (b) at least one organic or inorganic salt, of ammonium or of a monovalent or polyvalent metal cation; and by physical crosslinking of the said polymer resulting from hydrogen interactions between the functional groups of the said polymer and the water molecules in the hydration sphere of the said hydrated cation, for the preparation of cosmetic or dermatological compositions.

The invention relates more particularly to the use of the said coating agent for make-up products, in particular foundations, lipsticks, mascaras, eyeliners and care bases for the nails; for hair formulations, in particular styling products and/or products for holding the hair, or alternatively for skincare products.

30 Claims, No Drawings

USE OF A HYBRID POLYMERIC MATERIAL FOR COATING KERATINOUS MATERIALS

The present invention relates to cosmetic or dermatological compositions containing an agent capable of forming, on a keratin support, after drying, a deposit or a film consisting of a hybrid polymer material, as well as its various applications as an agent for coating keratin substances, in particular in the field of hair products and in the field of make-up products.

Throughout the description, the term "keratin substances" will be understood to mean substances to be cosmetically or dermatologically treated chosen from the skin, the scalp, the hair, the eyelashes, the eyebrows, the nails and mucous membranes.

Throughout the description, the expression "agent for coating keratin substances" will be understood to mean any material capable of forming a film or a deposit on a keratin support.

Many cosmetic applications make use of the transport of a water-soluble polymer which needs to give, after drying, on the keratin substance to be treated, a deposit or a film which has mechanical and cosmetic characteristics that are specific for the use envisaged. This is the case, for example, for many aqueous make-up products such as aqueous nail varnishes or mascaras and aqueous lipsticks or foundations. This is also the case for many hair products intended for holding the hair style, such as styling gels, mousses and lotions. Finally, this is the case for certain skincare products.

One of the aims of the present invention is to search for, in the context of make-up products for the face, in particular foundations, a novel coating polymer material which gives, after evaporation of the solvent medium, an extremely flexible film which is easy to deform under the action of the facial movements without producing a sticky feel and without transferring onto another support. Conventional foundations generally transfer colour and material by contact or rubbing on a support (fabrics, skin, etc.). Most of the solutions provided to solve this problem make use of polymers which form, after evaporation of the solvent medium, a film on the skin which adhesively bonds and imprisons the pigments. It is very difficult to obtain a deposit on the skin which is both effective, sufficiently flexible so as not to cause discomfort, non-sticky and transfer-resistant.

Another aim of the invention is to be able to make aqueous sticks of lipstick, based on a suitable coating polymer material, which can be manufactured easily by extrusion without heating, are homogeneous, stable and have satisfactory properties of rigidity, hardness, rheofluidization and transparency. A novel coating agent for the lips is also sought which applies easily to the lips and gives a homogeneous, flexible, comfortable, non-sticky, transfer-resistant film which is resistant to water, to saliva and to fatty substances and which has a moisturizing effect, providing moisture, freshness and softness.

Another aim of the present invention is thus to search for, in the context of aqueous mascaras, a novel polymer material for coating the eyelashes which produces, after drying, effects of maintenance, coverage and coloration of the eyelashes which are both resistant to water, to ambient humidity, to washing with aqueous solutions of surfactants and to conventional oil-based make-up-removing products for the face and resistant to dry rubbing (passing the hand over the eyelashes). This same coating material must be able to adhere easily to the eyelashes and to be distributed easily and homogeneously along the eyelashes, without leaving a sticky effect and without transferring. Conventional mascaras do not generally allow all of these aims to be achieved. Formulations based on this material are also sought which have a suitable rheofluidizing nature (fluidization under shear) in order to correctly coat and set the eyelashes all the way to the tip in order to obtain a genuine elongation of the eyelash.

Another aim of the invention is to be able to make aqueous gels for fixing and/or shaping the hair, based on a suitable coating polymer, which has rheological properties which allow the product to be taken up conveniently with the fingers, ease of spreading on the hair and homogeneous and uniform deposition along the fibres. In the context of styling products such as gels, lotions or mousses, a novel coating agent for the hair is also sought which gives a homogeneous, sufficiently flexible or even elastomeric, non-sticky film with good adhesive properties, which is able in particular to withstand ambient humidity (rain) or even shampooing several times depending on the desired cosmetic effect, and which gives a persistent wet look on the hair. The film-forming polymer systems or deposit systems commonly used in conventional styling products do not generally allow all of these aims to be achieved.

Hybrid materials consisting of a crosslinked network obtained by complexing at least one metal cation with at least one water-soluble polymer bearing functional groups capable of forming hydrogen bonds, such as sugars, oligosaccharides, polysaccharides or cellulose derivatives, are known in the prior art; the crosslinking results from hydrogen interactions between the functional groups and the water molecules in the hydration sphere of the hydrated metal cation. In particular, U.S. Pat. No. 4,506,684 describes crosslinked cellulose materials of this type which are intended for the manufacture of tobacco substitutes or additives in cigarettes. Materials of this type have been studied in the following articles:

Bain, Carbohydrate Research,84, 1–12 (1980): "An NMR study of the interaction between cadoxen and saccharides".

Misra, Vishnu, Carbohydrate Research, 59, 35–46 (1977): "Studies on electrolyte/non-electrolyte interactions; viscosity behaviour of alkali halides in aqueous solutions".

Kesting, J. of Applied Polymer Science, Vol. 9, p. 663–88 (1965).

Rendleman, Advances in Carbohydrate Chemistry & Biochemistry, 21, p. 209–271 (1966).

Burger, Biocoord. Chem. (1990) p. 236–83.

The Applicant has discovered, surprisingly, that this type of hybrid polymer material constitutes a noteworthy agent for coating keratin substances, which makes it possible to achieve all of the aims of the invention which have been listed above and which can be used in many forms of cosmetic and dermatological formulations, in particular in hair products, in make-up products and in skincare products.

The main subject of the invention is thus the use, for coating keratin substances, of a hybrid polymer material which can be obtained from an aqueous solution containing:

(a) at least one water-soluble polymer containing at least functional groups capable of forming hydrogen bonds, and (b) at least one cosmetically acceptable organic or inorganic salt, of ammonium or of a monovalent or multivalent metal cation; and by physical crosslinking of the said polymer resulting from hydrogen interactions between the said functional groups of the said polymer and the water molecules in the hydration sphere of the said hydrated cation, for the preparation of cosmetic or dermatological compositions.

Another subject relates to cosmetic and dermatological compositions containing, in a cosmetically acceptable medium, at least one agent which forms, after application to keratin substances, a film or a deposit consisting of a hybrid polymer material as defined above.

Other subjects will become apparent on reading the description and the examples which follow.

In order to obtain a crosslinking network by hydrogen bonds between the functional groups of the water-soluble polymer and the water molecules in the hydration sphere of the solvated cation, the proportion of ammonium or metal cation salt relative to the weight of the polymer will generally need to be equal to at least 50% by weight, but will not need to exceed the value corresponding to the saturation limit of the electrolyte in water, at the temperature at which the polymer/ammonium or metal cation salt mixture is used. This temperature generally ranges from 100° to 180° C. and more preferably from 20° to 100° C.

According to one specific form of the invention, in order to obtain on the keratin support a film or a deposit which is more resistant to water, to ambient humidity, to washing with aqueous solutions of surfactants or to conventional oil-based make-up-removing agents for the face, the coating agent used will be a hybrid polymer material in which the water-soluble polymer will also contain in its structure anionic or amphoteric functional groups which will give, in addition to the first crosslinking network by hydrogen bridging, a second crosslinking network resulting from ionic interactions between the ionic functional groups and a cation, preferably a multivalent metal cation. The said cation which participates in the formation of the second crosslinking network by ionic bridging may be the same as the one which participates in the formation of the first crosslinking network by hydrogen bridging or it may be derived from another ammonium or metal cation salt.

The salts of the invention are preferably chosen from cosmetically acceptable inorganic or organic salts of an alkali metal such as $Li^+$, $Na^+$, $K^+$; of an alkaline-earth metal such as $Ba^{2+}$, $Mg^{2+}$, $Ca^{2+}$, $Sr^{2+}$ or of a metal chosen from $Al^{3+}$, $Mn^{2+}$, $Zn^{2+}$, $Fe^{2+}$, $Fe^{3+}$, $Cu^{2+}$, $Ce^{4+}$, $Zr^{2+}$, $Ti^{2+}$, $Bi^{3+}$, $Ni^{2+}$, $V^{3+}$, $V^{4+}$, $V^{5+}$ or ammonium ($NH_4^+$).

The inorganic salts are chosen, for example, from the halides such as the chlorides, bromides, iodides and fluorides; the sulphates; the chlorates; the phosphates; the nitrates; the carbonates; the bicarbonates; the nitrites; the perchlorates; the periodates and the sulphonates.

The organic salts are chosen, for example, from the acetates, gluconates, tartrates, citrates, lactates, formates, thiocyanates, succinates, glycolates, malonates, dichloroacetates, oxalates, malates, adipates, fumarates, itaconates, maleates, butyrates, propionates, glycinates, carbamates, salicylates, thiosalicylates, pyruvates, sulphoxylates, thiosulphates, thiolates, benzoates and amino acid salts, in particular the glutamates and aspartates.

The water-soluble polymers used according to the invention to form the coating material are preferably chosen from natural polymers, modified natural polymers or synthetic polymers containing hydrogen bond acceptor/donor functional groups such as OH, COOH, amino, amide, urea, urethane, ether, thiol, amino acid or peptide.

Mention may be made in particular of cellulose polymers, polysaccharides, proteins or polypeptides and certain synthetic polymers.

Among the cellulose polymers according to the invention, mention may be made of water-soluble cellulose or starch ethers or esters, such as methylcellulose, hydroxyethylcellulose, hydroxypropylcellulose, methylhydroxyethylcellulose, methylhydroxypropylcellulose, ethylhydroxyethylcellulose, ethylhydroxypropylcellulose or carboxymethylcellulose in acid or salified form.

Among the polysaccharides according to the invention, mention may be made of:
plant gums such as guar gum, hydroxyethylguar or hydroxypropylguar, hydroxyalkylated guar gums bearing cationic groups, (non)hydroxyalkylated carboxymethylguars, carob gum, tara gum, gum arabic, karaya gum, ghatti gum, tamarind gum or gum tragacanth,
algal extracts such as carrageenans, alginates, agar agar or agarose,
pectins,
konjac and glucomannans,
polysaccharides of microbial origin, such as xanthan gums, dextrans, pullulans, gellans and derivatives thereof, shizophyllans or curdlans,
(non)acetylated chitosans,
hyaluronic acid.

Among the water-soluble proteins according to the invention, mention may be made of gelatin, collagen, elastin, glycosaminoglycans and polyamino acids.

Among the synthetic water-soluble polymers according to the invention bearing hydrogen bond donor/acceptor groups and optionally anionic or amphoteric groups, mention may be made of:
vinyl alcohol homopolymers and copolymers;
homopolymers or copolymers of ethylene oxide, in particular with monomers such as propylene oxide or methylene oxide;
water-soluble acrylic or methacrylic acid homopolymers or copolymers;
water-soluble homopolymers or copolymers of hydroxyethyl (meth)acrylate, 2-hydroxypropyl (meth)acrylate, (meth)acrylamide, N,N-dimethylacrylamide or N-isopropylacrylamide;
water-soluble polyolefins;
vinylpyrrolidone or vinylcaprolactam homopolymers or copolymers;
water-soluble polyesters or polyesteramides or polyamides;
water-soluble polyurethanes or polyureas or urea/urethane copolymers;
water-soluble silicones;
water-soluble polyamines.

The hybrid coating materials according to the invention can be prepared by mixing together and dissolving, at room temperature or under warm conditions, using a conventional stirring device (Raineri, Moritz or Ultra-Turrax type shearing dispersion or by extrusion) in an aqueous solution, the water-soluble polymer bearing hydrogen bond donor/acceptor groups, the electrolyte or an electrolyte mixture comprising the metal cation(s) capable of participating in the crosslinking by hydrogen bridging and optionally in the crosslinking by ionic bridging of the polymer. The implementation temperature will depend on the dissolution characteristics of the polymer and/or of the electrolyte(s).

Another subject of the invention consists of cosmetic or dermatological compositions containing, in a cosmetically acceptable aqueous medium, at least one agent which forms, after application to keratin substances, a coating consisting of a hybrid polymer material as defined above. The cosmetically acceptable aqueous medium for the compositions of the invention preferably consists of water or of a mixture of water and at least one cosmetically acceptable solvent which is compatible with the coating agent, such as a monoalcohol, a polyalcohol, a glycol ether, acetone or an ester, alone or in the form of a mixture. It more particularly consists of water or of water and a lower $C_1$–$C_4$ alcohol such as ethanol or isopropanol.

The compositions according to the invention can be in any form which is suitable for topical application, in particular in the form of solutions of the lotion or serum type; in the form of aqueous gels; in the form of emulsions obtained by dispersing a fatty phase in an aqueous phase (O/W) or, conversely, (W/O), of more or less thickened liquid consistency such as milks, or more or less unctuous creams, or in solid form such as a stick. These compositions are prepared according to the usual methods.

The coating agents according to the invention are present in the compositions in accordance with the invention in solids concentrations preferably ranging from 0.1 to 60% by weight of solids, and more preferably from 0.5 to 40% by weight, relative to the total weight of the composition. The concentration of coating agent will depend on the cosmetic or dermatological application envisaged.

In a known manner, all the compositions of the invention can contain adjuvants that are common in the cosmetics and dermatological fields, such as oils, waxes or other common fatty substances, conventional gelling and/or thickening agents; emulsifiers; moisturizers; emollients; sunscreens; hydrophilic or lipophilic active agents such as ceramides; anti-free-radical agents; surfactants; polymers; proteins; bactericides; sequestering agents; anti-dandruff agents; antioxidants; preserving agents; basifying or acidifying agents; fragrances; fillers; dyestuffs. The amounts of these various adjuvants are those used conventionally in the fields considered.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

According to one specific form of the invention, the compositions according to the invention can contain cosmetic or dermatological active agents which are physically imprisoned in the matrix of the hybrid material, i.e. linked by ionic and/or hydrogen bonds to the hybrid material. These active agents may be chosen from any water-soluble or water-dispersible agent which is found trapped in the final film or coating formed. These active agents can be, for example, water-soluble anionic dyes whose cationic counterion participates in the physical crosslinking of the polymer, (non)coloured organic or inorganic pigments, anti-irritant cations such as strontium, etc.

The hair compositions according to the invention are preferably styling products such as hair setting gels or lotions, blow-drying lotions and fixing and styling products such as lacquers or sprays. The lotions can be packaged in various forms, in particular in vaporizers, pump-dispenser bottles or in aerosol cans in order to apply the composition in vaporized form or in the form of a mousse. Such packaging forms are indicated, for example, when it is desired to obtain a spray or a mousse for fixing or treating the hair. The hair compositions according to the invention can also provide temporary coloration to the hair. This is possible because the hybrid coating material can trap in its matrix one or more dyes or one or more organic or inorganic pigments by ionic and/or hydrogen bonds.

The compositions of the invention can also be used as care, treatment or protective products for the skin, in particular for the face, for the hands or for the body, such as, for example, deodorant products in the form of sticks.

The compositions can be make-up products and more particularly foundations, mascaras, eyeliners, lipsticks or care bases for the nails. The compositions of the invention can be transfer-resistant make-up products.

Another subject of the invention is a process for the non-therapeutic, cosmetic treatment of the skin, the scalp, the hair, the eyelashes, the eyebrows, the nails or mucous membranes, characterized in that a composition as defined above is applied to the keratin support according to the usual technique for using this composition.

The examples which follow serve to illustrate the present invention without, however, being limiting in nature.

EXAMPLE 1

Styling Gel

A gel having the composition below is prepared:

| | |
|---|---|
| Carob gum | 2% by weight |
| $CaCl_2$ | 2% by weight |
| Water | qs 100% by weight |

Procedure 20 g of carob gum powder are dispersed in 920 ml of water at room temperature using a deflocculating machine such as a Rayneri mixer, in a 2-liter reactor. The powdered gum is introduced slowly over 5 minutes at 850 revolutions/minute. The mixture is stirred for 15 minutes at 850 revolutions/minute. The aqueous dispersion is then heated to 80° C. while stirring is continued. An aqueous $CaCl_2$ solution obtained by dissolving 20 g of dehydrated salt in 60 ml of water is added dropwise. The mixture is stirred at 80° C. for 60 min. A transparent gel is thus obtained.

Comparative Example 2
(Not Forming Part of the Invention)

A gel having the composition below is prepared:

| | |
|---|---|
| Carob gum | 2% by weight |
| Water | qs 100% by weight |

Procedure

The process is performed under the same conditions as those of Example 1, without the step of adding the $CaCl_2$ solution. A viscous and transparent solution is again obtained.

Sensory Styling Tests 1.5 g of the styling gel of Example 1 and 1.5 g of the gel of Comparative Example 2 are applied, respectively, to one half of the head, on 10 individuals. These three individuals judged that the styling gel of Example 1 had better properties than that of Example 2 in terms of:

the sheen, the body, the holding of the hair, the softness to the touch of the hair.

EXAMPLE 3

Transparent Aqueous Hygiene or Care Stick

A stick having the composition below is prepared:

| | |
|---|---|
| Carob gum | 20% by weight |
| $CaCl_2$ | 20% by weight |
| Water | qs 60% by weight |

Procedure

The following process is performed in a 6-zone extruder with a flow rate of 3 kg/h.

Zone 1: The carob powder is introduced at 100° C.;
Zone 2: The water is introduced at 100° C.;
Zones 3 and 4: The carob and the water are mixed together at 120° C.;
Zone 5: A 30% $CaCl_2$ solution is introduced at 120° C.;
Zone 6: The stick is extruded at 95° C.

A transparent stick with a fresh, pleasant feel is obtained.

Comparative Example 4
(Not Forming Part of the Invention)

An aqueous stick having the composition below is prepared:

| | |
|---|---|
| Carob gum/carrageenan mixture (50/50 by weight) | 33% by weight |
| Water | 67% by weight |

Procedure

The following process is also performed in a 6-zone extruder with a flow rate of 3 kg/h.
Zone 1: The carob/carrageenan mixture is introduced at 100° C.;
Zone 2: The water is introduced at 100° C.;
Zones 3 to 5: The carob/carrageenan mixture and the water are mixed together at 120° C.;
Zone 6: The stick is extruded at 95° C.

Compared with the product of Example 3, a less rigid, less transparent stick with a less pleasant feel and a less pronounced sensation of freshness is obtained.

What is claimed is:

1. A method of preparing a cosmetic and/or dermatological composition comprising the step of including in said composition a hybrid polymer material obtained from an aqueous solution comprising:
   (a) at least one water-soluble polymer comprising functional groups capable of forming hydrogen bonds, and
   (b) at least one cosmetically and/or dermatologically acceptable salt selected from organic and inorganic salts of ammonium cation and of monovalent and multivalent metal cations, wherein water molecules form a hydration sphere of said cation(s) and further wherein a first physical crosslinking networking via hydrogen interaction occurs between said functional groups of said at least one water-soluble polymer and said water molecules in said hydration sphere of said cation(s).

2. A method for coating a keratin substance, comprising coating said keratin substance with a hybrid polymer material obtained from an aqueous solution comprising:
   (a) at least one water-soluble polymer comprising at least one functional group capable of forming hydrogen bonds, and
   (b) at least one cosmetically and/or dermatologically acceptable salt selected from organic and inorganic salts of ammonium cation and of monovalent and multivalent metal cations, wherein water molecules form a hydration sphere of said cation(s) and further wherein a first physical crosslinking network via hydrogen interaction occurs between said functional groups of said at least one water-soluble polymer and said water molecules in said hydration sphere of said cation (s).

3. A method according to claim 1, wherein the proportion of said at least one cosmetically and/or dermatologically acceptable salt relative to the weight of said at least one water-soluble polymer is at least 50% by weight, and does not exceed the saturation limit of said salt in water at the temperature at which said at least one cosmetically and/or dermatologically acceptable salt and said at least one water-soluble polymer are combined.

4. A method according to claim 3, wherein said temperature ranges from 10° to 100° C.

5. A method according to claim 4, wherein said temperature ranges from 20° to 100° C.

6. A method according to claim 1, wherein said at least one water-soluble polymer further comprises additional functional groups selected from anionic and amphoteric groups and wherein said additional functional groups form a second crosslinking network via ionic interactions between said additional functional groups and said cation(s).

7. A method according to claim 1, wherein said at least one cosmetically and/or dermatologically acceptable salt is selected from alkali metal, alkaline-earth metal, $Al^{3+}$, $Mn^{2+}$, $Zn^{2+}$, $Fe^{3+}$, $Cu^{2+}$, $Ce^{4+}$, $Zr^{2+}$, $Ti^{2+}$, $Bi^{3+}$, $N^{i2+}$, $V^{3+}$, $V^{4+}$, $V^{5+}$, and ammonium salts.

8. A method according to claim 1, wherein said at least one cosmetically and/or dermatologically acceptable salt is selected from halides, sulphates, chlorates, phosphates, nitrates, carbonates, bicarbonates, nitrites, perchlorates, periodates, and sulphonates.

9. A method according to claim 1, wherein said at least one cosmetically and/or dermatologically acceptable salt is selected from acetates, gluconates, tartrates, citrates, lactates, formates, thiocyanates, succinates, glycolates, malonates, dichloroacetates, oxalates, malates, adipates, fumarates, itaconates, maleates, butyrates, propionates, glycinates, carbamates, salicylates, thiosalicylates, pyruvates, sulphoxylates, thiosulphates, thiolates, benzoates and amino acid salts.

10. A method according to claim 9, wherein said amino acid salts are selected from glutamate and aspartate.

11. A method according to claim 1, wherein said at least one water-soluble polymer is a polymer containing hydrogen bond acceptor/donor functional groups.

12. A method according to claim 11, wherein said hydrogen bond acceptor/donor functional groups are selected from OH, COOH, thiol, amino, amide, urea, urethane, ether, amino acid and peptide.

13. A method according to claim 1, wherein said at least one water-soluble polymer is selected from natural and modified celluloses, starch ethers, and starch esters, natural and modified polysaccharides, proteins of plant and animal origin and synthetic polymers.

14. A method according to claim 1, wherein said at least one water-soluble polymer is selected from methylcellulose, hydroxyethylcellulose, hydroxypropylcellulose, methylhydroxyethylcellulose, methylhydroxypropylcellulose, ethylhydroxyethylcellulose, ethylhydroxypropylcellulose and carboxymethylcellulose in acid and salified forms, guar gum, hydroxyethylguar, hydroxypropylguar, hydroxyalkylated guar gums bearing cationic groups, (non)hydroxyalkylated carboxymethylguar, carob gum, tara gum, gum arabic, karaya gum, ghatti gum, tamarind gum, gum tragacanth, carrageenan, alginate, agar agar, agarose, pectin, konjac, glucomannan, xanthan gum, dextran, pullulan, gellan, shizophyllan, curdlan, (non)acetylated chitosan, hyaluronic acid, gelatin, collagen, elastin, glycosaminoglycan, polyamino acids, vinyl alcohol homopolymers and copolymers, homopolymers and copolymers of ethylene oxide, acrylic and methacrylic acid homopolymers and copolymers, homopolymers and copolymers of hydroxyethyl (meth)acrylate, 2-hydroxypropyl (meth)acrylate, (meth)acrylamide, N,N-dimethylacrylamide and N-isopropylacrylamide, polyolefins, vinylpyrrolidone and vinylcaprolactam homopolymers and copolymers, polyesters, polyesteramides, polyamides, polyurethanes, polyureas, urea/urethane copolymers, silicones, and polyamines.

15. A method of forming a film, comprising applying at least one coating agent on a keratin substance, wherein said at least one coating agent forms a film after said application, and wherein said at least one coating agent comprises:

a hybrid polymer material obtained from an aqueous solution comprising:
(a) at least one water-soluble polymer comprising functional groups capable of forming hydrogen bonds, and
(b) at least one cosmetically and/or dermatologically acceptable salt, said salt being selected from organic and inorganic salts of ammonium cation and of monovalent and multivalent metal cations, wherein water molecules form a hydration sphere of said cation(s) and further wherein a first physical crosslinking networking via hydrogen interaction occurs between said functional groups of said at least one water-soluble polymer and said water molecules in said hydration sphere of said cation(s).

16. A cosmetic and/or dermatological composition, comprising, in a cosmetically and/or dermatologically acceptable aqueous medium, at least one coating agent which coats keratin substances, said at least one coating agent comprising:

a hybrid polymer material obtained from an aqueous solution comprising:
(a) at least one water-soluble polymer comprising functional groups capable of forming hydrogen bonds, and
(b) at least one cosmetically and/or dermatologically acceptable salt, said salt being selected from organic and inorganic salts of ammonium cation and of monovalent and multivalent metal cations, wherein water molecules form a hydration sphere of said cation(s) and further wherein a first physical crosslinking networking via hydrogen interaction occurs between said functional groups of said at least one water-soluble polymer and said water molecules in said hydration sphere of said cation(s).

17. A composition according to claim 16, wherein said cosmetically and/or dermatologically acceptable aqueous medium is water or a mixture of water and at least one cosmetically and/or dermatologically acceptable solvent, and wherein said at least one cosmetically and/or dermatologically acceptable solvent is compatible with said hybrid polymer material.

18. A composition according to claim 17, wherein said at least one cosmetically and/or dermatologically acceptable solvent is selected from monoalcohols, polyalcohols, glycols, ethers, acetones, and esters.

19. A composition according to claim 16, wherein the amount of said at least one coating agent ranges from 0.1 to 60% by weight of solids, relative to the total weight of the composition.

20. A composition according to claim 19, wherein the amount of said at least one coating agent ranges from 0.5 to 40% by weight of solids, relative to the total weight of the composition.

21. A composition according to claim 16, further comprising at least one cosmetic and/or dermatological active agent.

22. A composition according to claim 21, wherein said at least one cosmetic and/or dermatological active agent is linked to said hybrid polymer material by hydrogen or ionic bonds.

23. A composition according to claim 16, wherein said composition is a hair product.

24. A composition according to claim 23, wherein said composition is a hair product for holding the hair style or for shaping the hair.

25. A composition according to claim 16, wherein said composition is a care, treatment and/or protective product for the skin.

26. A composition according to claim 16, wherein said composition is a make-up product.

27. A composition according to claim 26, wherein said composition is a foundation, a mascara, an eyeliner, a lipstick or a care base for the nails.

28. A composition according to claim 26, wherein said composition is a transfer-resistant make-up product.

29. A composition according to claim 16, wherein said composition is in the form of a lotion, an aqueous gel, an emulsion, a cream, or a solid.

30. A method for the non-therapeutic, cosmetic treatment of the skin, the scalp, the hair, the eyelashes, the eyebrows, the nails or mucous membranes, comprising applying an effective amount of said composition according to claim 16 to said skin, scalp, hair, eyelashes, eyebrows, nails or mucous membranes to achieve said treatment.

* * * * *

UNITED STATES PATENT AND TRADEMARK OFFICE
CERTIFICATE OF CORRECTION

PATENT NO.     : 6,436,412 B1
DATED          : August 20, 2002
INVENTOR(S)    : Francis Quinn It is certified that error appears in the above-identified patent and that said Letters Patent is hereby corrected as shown below:

Column 8,
Line 7, "100º C." should read -- 180º C. --.

Signed and Sealed this

Twelfth Day of November, 2002

Attest:

Attesting Officer

JAMES E. ROGAN
Director of the United States Patent and Trademark Office